US00PP28614P2

(12) United States Plant Patent
Hansen

(10) Patent No.: US PP28,614 P2
(45) Date of Patent: Nov. 7, 2017

(54) X MANGAVE PLANT NAMED 'KALEIDOSCOPE'

(50) Latin Name: ***Manfreda×Agave* hybrid**
Varietal Denomination: Kaleidoscope

(71) Applicant: Hans A. Hansen, Zeeland, MI (US)

(72) Inventor: Hans A. Hansen, Zeeland, MI (US)

(73) Assignee: Walters Gardens Inc, Zeeland, MI (US)

( * ) Notice: Subject to any disclaimer, the term of this patent is extended or adjusted under 35 U.S.C. 154(b) by 84 days.

(21) Appl. No.: 14/999,083

(22) Filed: Mar. 29, 2016

(51) Int. Cl.
*A01H 5/12* (2006.01)

(52) U.S. Cl.
USPC ..... Plt./373

(58) Field of Classification Search
USPC ..... Plt./373
See application file for complete search history.

*Primary Examiner* — Susan McCormick Ewoldt
*Assistant Examiner* — Karen Redden

(57) ABSTRACT

A new and unique X Mangave plant named 'Kaleidoscope' characterized by long arching succulent foliage with blue-green centers and variegated yellowish-green to yellowish-cream margins developing under ultra violet light grey-purple to cherry red speckling throughout and strong cherry-red tinting in the margin. The green flowers on tall stiff scapes are loaded with nectar are highly attractive to hummingbirds.

1 Drawing Sheet

Botanical classification: *Manfreda×Agave* hybrid.
Variety denomination: 'Kaleidoscope'.

BACKGROUND OF THE INVENTION

The present invention relates to the new and distinct X Mangave plant, X Mangave 'Kaleidoscope' discovered by the inventor at a wholesale perennial nursery in Zeeland, Mich., USA as an uninduced whole-plant mutation in a tissue cultured crop of X Mangave 'Jaguar' (not patented) the Sep. 1, 2013. Through trials at the same nursery since that discovery the plant was referred to by the code 13-SP-Manf-285-9. The new plant has been successfully asexually propagated initially by division at the same nursery in Zeeland, Mich. and also by tissue culture. Both methods of asexual propagation systems have been found to produce stable and identical plants that maintain all the unique characteristics of the original plant.

No plants of X Mangave 'Kaleidoscope' have been sold, in this country or anywhere in the world, prior to the filing of this application, nor has any disclosure of the new plant been made prior to the filing of this application with the exception of that which was disclosed within one year of the filing of this application, and was either derived directly or indirectly from the inventor.

BRIEF SUMMARY OF THE INVENTION

X Mangave 'Kaleidoscope' differs from its parent, 'Jaguar', as well as all other *Manfreda, Agave* and X Mangave known to the applicant. The most similar known X Mangave cultivar is 'Expresso' (not patented). 'Expresso' is a chimera sport of X Mangave 'Macho Mocha', which is a sport of *Manfreda variegata×Agave celsii* (not patented) presumably. 'Jaguar' is a chimera sport of *Manfreda guttata* and an unknown *Agave*. The variegation differs in that 'Expresso' is lighter cream to near white on the margin, whereas the variegation of 'Kaleidoscope' is a light lemon-green that develops more larger speckles and a cherry-red coloration on the margin and the leaves are narrower and not as thick adaxial to abaxial. Other similar X Mangave with chimera variegation include: 'Cappuccino' (not patented) with a lighter green center and blue-green margin; 'Bloodspot' PDN with edge (Avent) (not patented) has much shorter less arching foliage and the margin is nearly creamy white. There are numerous variegated *Agave* known to the inventor including *Agave* 'Desert Diamond' U.S. Plant Pat. No. 26,384 with a very compact habit and rigid spiny leaves and bright cream margin.

The new plant, 'Kaleidoscope', is unique from all of these variegated *Agave*, X Mangave and *Manfreda* known to the inventor by the following combined traits:

1. Long, arching, succulent foliage with blue-green centers and variegated yellowish-green to yellowish cream margins;
2. Foliage develops greyed-purple to cherry-red speckling throughout and strong cherry-red tinting in the margin;
3. Moderate to rapid growth rate with good natural pup production;
4. Flowers on stiff, tall, lightly-branched scapes.

BRIEF DESCRIPTION OF THE DRAWINGS

The photograph of the new plant demonstrates the overall appearance of the new plant including the unique traits as a two-year-old plant grown in a container in a greenhouse with supplemental water and fertilizer as needed. The colors are as accurate as reasonably possible with color reproductions. Ambient light spectrum, temperature, source and direction may cause the appearance of minor variation in color.

DETAILED BOTANICAL DESCRIPTION

Figure 1:
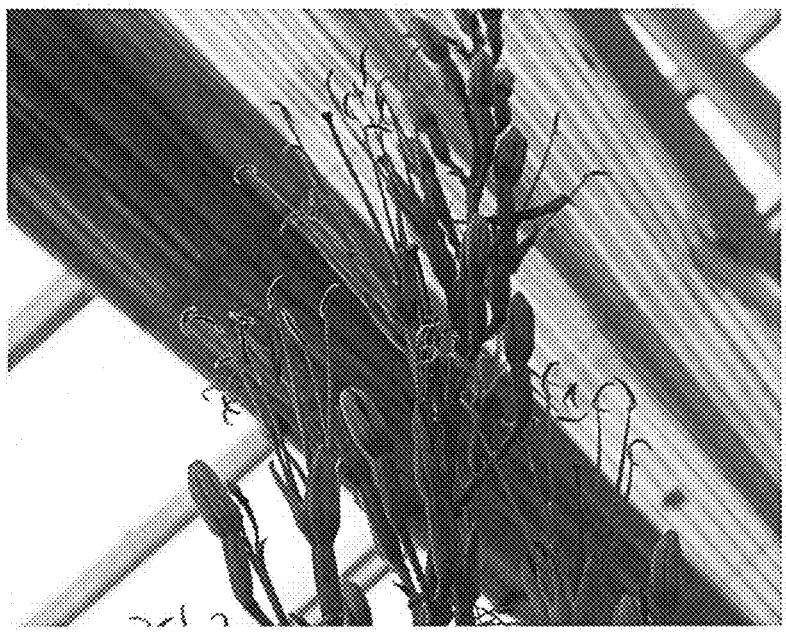
FIG. 1 shows a close-up of the flowers and buds.
Figure 2:
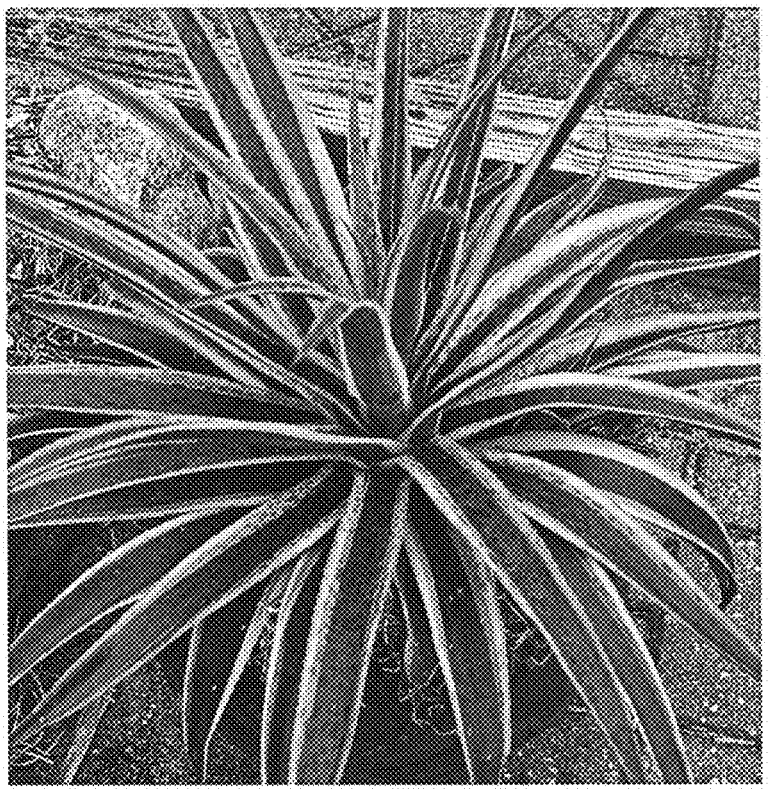
FIG. 2 shows the new plant in a container prior to flowering.

The following descriptions and color references are based on the 2001 edition of The Royal Horticultural Society Colour Chart except where common dictionary terms are used. The new plant, X Mangave 'Kaleidoscope', has not been observed under all possible environments. The phenotype may vary slightly with different environmental conditions, such as temperature, light, fertility, moisture and maturity levels, but without any change in the genotype. The following observations and size descriptions are of a two-year old plant in a commercial wholesale greenhouse in Zeeland, Mich. with supplemental water and fertilizer as needed.

Botanical classification: X Mangave hybrid.

Variety denomination: 'Kaleidoscope'.

Sport parentage: Uninduced whole-plant chimeral sport of X Mangave 'Jaguar'.

Propagation: Division and sterile plant tissue culture.

Time to initiate roots from tissue culture: About 21 days.

Growth rate: Moderate to rapid.

Crop time: About 12 to 16 weeks to finish during lengthening spring days from an established 25 mm tissue culture plug to a 65 mm diameter container.

Rooting habit: Fleshy, lightly branching, with roots up to 15 cm long.

Root color: Nearest RHS 158C.

Plant shape and habit: Succulent herbaceous perennial with basal rosettes of about 50 fleshy leaves radially emerging and arching from central rhizome, producing a symmetrical rounded mound.

Plant size: Foliage height about 45.0 cm tall from soil line to the top of the leaves and about 72.0 cm wide at the widest point at soil line.

Foliage description: Gladiate to lanceolate; simple, fleshy, glabrous; margins finely dentate with flexible teeth; apex acute with mucro; base truncate, sessile, clasping.

Number of leaves: About 50 per plant.

Leaf blades: Finely dentate; to about 35.0 cm long, about 4.7 cm wide at base and 4.0 mm thick, average about 32.5 cm long, 4.0 cm wide and 4.0 mm thick; usually bi-laterally symmetrical; glabrous and glaucous above and below; variegation with wide margin about 1.4 cm wide near base; with intermediate lighter green zone between margin and center on older leaves of about 7.0 mm wide at widest point and irregular speckles of between about 1.0 diameter to about 3.0 mm across and about 6.0 mm long.

Foliage fragrance: None observed.

Leaf blade color:

*Adaxial* (*young*) *center*.—Nearest RHS 135C with speckles nearest RHS N187A.

*Abaxial* (*young*) *center*.—Between RHS 139C and RHS 139B with speckles nearest RHS N187A.

*Adaxial* (*young*) *margin*.—Nearest RHS 151A with speckles of nearest RHS N187A.

*Abaxial* (*young*) *margin*.—Nearest RHS N144A with speckles of nearest RHS N187A.

*Adaxial* (*mature*) *center*.—Between RHS 126A and RHS 133A with speckles of nearest RHS N187A.

*Abaxial* (*mature*) *center*.—More green than RHS 126B and more blue than RHS 133B with speckles of nearest RHS N187A.

*Adaxial* (*mature*) *margin*.—Between RHS 126A and RHS 133A and frequently developing red coloring or tinting with intense ultra violet light of nearest RHS 53B and with speckles of nearest RHS 187B.

*Abaxial* (*mature*) *margin*.—Between RHS 126A and RHS 133A and frequently developing red coloring or tinting of nearest RHS 53B and with speckles of nearest RHS 187B.

*Adaxial intermediate zone*.—Ranging between RHS 133D and a blend between RHS N187B and RHS 186B with speckles of nearest RHS 184B.

Mucro: Flexible; straight, about 1.0 cm long.

Mucro color: Nearest RHS 200A.

Spine texture: Flexible, glabrous, sharply pointed.

Petiole: Sessile.

Veins: Parallel; not distinct.

Peduncle: Terete; glaucous; glabrous; stiff; strong; with cauline leaves nearly adpressed along surface; about 260 cm long and 2.0 cm diameter at base; attitude upwards, erect.

Peduncle color: With glaucous bloom nearest RHS N138A, without glaucous bloom nearest RHS 139A.

Pedicel: Terete; glaucous; glabrous; stiff; strong; about 1.7 cm long and 2.5 mm diameter.

Pedicel color: Nearest RHS 138A.

Cauline leaves: About 29 per scape; gladiate to lanceolate; simple, fleshy, glabrous; margins finely dentate with flexible teeth; apex acute with mucro; base truncate, sessile, clasping; proximally about 32.5 cm long and about 1.5 cm wide at base, decreasing distally; color adaxial and abaxial same as basal leaves.

Buds one day prior to opening: Elongated globose; terminal bulb about 2.6 cm long and about 1.0 cm across; proximal tube about 2.4 cm long and 6.0 mm across; overall about 5.0 cm long.

Bud color: Nearest RHS 138A.

Flower description: Perfect, actinomorphic; about 11.0 cm long and opening to about 5.0 cm across at outside of anthers; lasting about 3 to 4 days per flower; flowering period about three weeks in late winter in Michigan greenhouse; producing abundant nectar; approximately 75 flowers per scape; attitude mostly upright.

Flower fragrance: Faintly sweet.

Tepals: Six; glaucous abaxial; glabrous both adaxial and abaxial; acute apex and fused base; in two sets of three; outer set about 2.8 cm long and about 5.0 mm wide at base; inner set about 2.8 cm long and 4.0 mm wide at base; inner set creased along edge where overlapped with outer set while in bud.

Tepal color: Outer set adaxial nearest RHS 146B, abaxial nearest RHS N138C with glaucous bloom and nearest RHS 138A with glaucous bloom removed; inner set adaxial nearest RHS 146A and margin between RHS 146A and RHS 144A, and abaxial nearest RHS N138C with glaucous bloom and nearest RHS 138A without glaucous bloom and nearest RHS 144A along creased margin.

Androecium: Six.

*Filaments*.—Six; stiff and straight; about 7.0 cm long and 2.0 mm diameter at base; color between RHS 145C and RHS 160C with dense speckling of nearest RHS 182A.

*Anther*.—Dorsifixed; longitudinal; about 2.2 cm long and 1.0 mm diameter before opening; after dehiscence curving backward; color nearest RHS 165A.

*Pollen*.—Abundant; color nearest RHS 18A.

Gynoecium: Single.

*Style*.—5.5 cm long and 2.0 mm diameter at base; color blend between RHS 145C and RHS 160C with dense speckling of RHS 184A.

*Stigma*.—Globose, apex tri-lobed; about 2.5 mm tall and 3.0 mm across top; color side and top between RHS 177A and RHS 187A; top stigmatic surface in tri-pointed star with color nearest RHS 194B.

*Ovary*.—Inferior.

Fruit: Dehiscent, tri-valved, loculicidal capsule; apex abruptly acute; base slightly tapered; about 3.5 cm long and 1.7 cm across.

Fruit color: When immature nearest RHS N138A; at dehiscence blend between RHS 199C and RHS 161B.

Seed: Flattened, near round; about 5.0 mm across and about 1.0 mm thick; color nearest RHS 202A.

Disease resistance: X Mangave 'Kaleidoscope' has not been observed to be resistant to diseases common to other X Mangave beyond that which is normal for *Agave* or *Manfreda*. The plant is xeromorphic and survives well with minimal water once established. Hardiness at least from USDA zone 8 to 11. Full extent of winter hardiness has not been tested.

I claim:

1. A new and distinct cultivar of ornamental X Mangave plant named 'Kaleidoscope' as herein described and illustrated, suitable as a potted plant or for the garden.

* * * * *